United States Patent
Bayram et al.

(10) Patent No.: US 7,649,354 B2
(45) Date of Patent: Jan. 19, 2010

(54) METHOD AND APPARATUS FOR ACQUIRING MAGNETIC RESONANCE IMAGING DATA

(75) Inventors: Ersin Bayram, Delafield, WI (US); Charles R. Michelich, Waukesha, WI (US); Anthony T. Vu, Waukesha, WI (US); Reed F. Busse, Madison, WI (US)

(73) Assignee: General Electric Co., Schenectady, NY (US)

( * ) Notice: Subject to any disclaimer, the term of this patent is extended or adjusted under 35 U.S.C. 154(b) by 295 days.

(21) Appl. No.: 11/861,916

(22) Filed: Sep. 26, 2007

(65) Prior Publication Data

US 2009/0082656 A1    Mar. 26, 2009

(51) Int. Cl.
*G01V 3/00*    (2006.01)
(52) U.S. Cl. ........................ 324/309; 324/307
(58) Field of Classification Search ............. 324/309, 324/307
See application file for complete search history.

(56) References Cited

U.S. PATENT DOCUMENTS

| | | | | |
|---|---|---|---|---|
| 6,694,165 | B2 * | 2/2004 | Zhu ........................ | 600/410 |
| 7,265,546 | B2 | 9/2007 | Kannengiesser et al. | |
| 7,265,547 | B2 | 9/2007 | Vu | |
| 7,382,127 | B2 * | 6/2008 | Gaddipati et al. ........... | 324/309 |
| 7,423,430 | B1 * | 9/2008 | Sharif et al. ................ | 324/309 |

2003/0011368 A1    1/2003 Abe

FOREIGN PATENT DOCUMENTS

WO    2004081597 A1    9/2004
WO    2006119164 A2    11/2006

OTHER PUBLICATIONS

Hu et al., The Combination of 2D Sense and 2D Partial Fourier Homodyne Reconstruction: Achieving Accelartion Factors Greater Than the Number of Coils, Proc. Intl. Soc. Mag. Reson. Med. 14 (2006).
Haider et al., Time-Resolved 3D Contrast-Enhanced MRA with 2D Homodyne and View Sharing for Contrast Bolus Dynamics of the Brain, Proc. Intl. Soc. Mag. Reson. Med. 14 (2006).
Hu et al., Parallel Imaging with Partial Fourier Acquisitions for 3D MRI, Proc. Intl. Soc. Mag. Reson. Med. 13 (2005).
Bernstein et al., Effect of Windowing and Zero-Filled Reconstruction of MRI Data on Spatial Resolution and Acquisition Strategy, Journal of Magnetic Resonance Imaging 14:270-280 (2001), Wiley-Liss, Inc.

* cited by examiner

*Primary Examiner*—Louis M Arana

(57)    ABSTRACT

A multi-shot three-dimensional (3D) magnetic resonance imaging (MRI) data view-ordering strategy for uniform or variable density k-space sampling schemes is presented. The $k_y$-$k_z$ plane is partitioned into multiple wedge-shaped "blades" (or radial fan beams). The angular size of individual blades may be adjusted according to the desired number of views for each blade. Each blade includes views near the origin that contain low-frequency information about the imaged object such that views having the most desirable characteristics may be used to fill the central portions of k-space.

24 Claims, 11 Drawing Sheets

METHOD AND APPARATUS FOR ACQUIRING MAGNETIC RESONANCE IMAGING DATA

TECHNICAL FIELD

The present invention relates generally to magnetic resonance imaging (MRI) systems and in particular, to a method and apparatus for view-ordering in a multi-shot three-dimensional MRI data acquisition.

BACKGROUND

Magnetic resonance imaging (MRI) is a medical imaging modality that can create images of the inside of a human body without using x-rays or other ionizing radiation. MRI uses a powerful magnet to create a strong, uniform, static magnetic field (i.e., the "main magnetic field"). When a human body, or part of a human body, is placed in the main magnetic field, the nuclear spins that are associated with the hydrogen nuclei in tissue water become polarized. This means that the magnetic moments that are associated with these spins become preferentially aligned along the direction of the main magnetic field, resulting in a small net tissue magnetization along that axis (the "z axis," by convention). A MRI system also comprises components called gradient coils that produce smaller amplitude, spatially varying magnetic fields when current is applied to them. Typically, gradient coils are designed to produce a magnetic field component that is aligned along the z axis and that varies linearly in amplitude with position along one of the x, y or z axes. The effect of a gradient coil is to create a small ramp on the magnetic field strength, and concomitantly on the resonance frequency of the nuclear spins, along a single axis. Three gradient coils with orthogonal axes are used to "spatially encode" the MR signal by creating a signature resonance frequency at each location in the body. Radio frequency (RF) coils are used to create pulses of RF energy at or near the resonance frequency of the hydrogen nuclei. These coils are used to add energy to the nuclear spin system in a controlled fashion. As the nuclear spins then relax back to their rest energy state, they give up energy in the form of an RF signal. This signal is detected by the MRI system and is transformed into an image using a computer and known reconstruction algorithms.

MRI data may be acquired using a three-dimensional (3D) acquisition strategy, the most common of which is a rectilinear sampling that fills a 3D Cartesian grid with Fourier reciprocal space (i.e., "k-space") data. The data may be collected with Nyquist frequency sampling to provide unique location encoding of the MRI signals and thereby prevent aliasing in the reconstructed images. The 3D data is spatially encoded using phase encoding along two perpendicular spatial directions (the y and z directions) and frequency encoding along the third (the x direction). Usually, the secondary phase encoding is referred to as "slice encoding," to distinguish it from the primary phase-encoding. The resultant raw data fills a 3D k-space matrix which is then "reconstructed" using Fourier transformation techniques, resulting in a stack of two-dimensional images.

To reduce acquisition time for 3D imaging, "parallel imaging" techniques (also known as "partially parallel imaging") may be used in which k-space is undersampled (i.e., the Nyquist criteria is not met) and the signals from multiple receiver coils are combined to provide aliasing free images. Other techniques, such as auto-calibrated (or self-calibrated) parallel imaging techniques, homodyne techniques, and zero-filling techniques may be used, all of which use non-uniform sampling in the $k_y$-$k_z$ plane, i.e., while some portions of k-space may be fully sampled at the Nyquist frequency, other portions may be undersampled or not sampled at all. Techniques such as auto-calibrated parallel imaging techniques, homodyne techniques, and zero-filling techniques may be referred to as "variable density" techniques, in which k-space is not sampled with uniform density of acquired views throughout. Variable density techniques may also be used for motion artifact reduction schemes or other purposes.

MRI data is typically collected in frames that are referred to as "views." Each view corresponds to a single $k_y$ and $k_z$ value, but contains data for the full range of $k_x$ values that are required to reconstruct an image. Multiple view-ordering schemes are known in the art for determining how $k_y$, $k_z$ encoding is performed for each view. For example, in a "nested" view-ordering scheme, all of the views corresponding to one phase-encoding axis ($k_z$, for example) are acquired before incrementing the value on the other phase-encoding axis ($k_y$, for example). An "elliptical centric" view-ordering scheme replaces the two nested loops with a single loop that steps through $k_y$, $k_z$ pairs according to their distance from the origin in the $k_y$-$k_z$ plane. The choice of a view-ordering scheme often depends on how the imaged object or its corresponding magnetization is expected to change during the data acquisition. Views near the center of k-space have the strongest effect on the overall image appearance, because most of the k-space information about an object is contained near the center of k-space. It is desirable to obtain the low-frequency views near the center of k-space when the imaged object or its magnetization is in a preferred state, for example, when an imaged object is relatively motionless or when the magnetization of the imaged object has evolved such that image contrast between two tissues of interest is near its maximum.

For most practical 3D imaging applications, it is not possible to obtain all of the views necessary to reconstruct an image in a single, uninterrupted acquisition. It is therefore frequently necessary to acquire 3D MRI data using multiple "shots," each of which acquires a subset of the total required views. In a multi-shot acquisition, each shot may be preceded by a triggering event, such as by the playing out of a magnetization preparation (e.g., an inversion RF pulse or a fat suppression RF pulse) or by the receipt of a cardiac or respiratory trigger. Views obtained during one particular time window of the shot may be preferred to other views. For example, it may be desirable to use cardiac gating techniques to time the MRI data acquisition to diastole, when the heart muscle is more quiescent. In this example, a cardiac gating pulse triggers the start of each shot and views acquired during diastole are preferred. In another example, a fat-selective inversion RF pulse may precede each shot and invert the longitudinal magnetization from fat. Views acquired in a window around the null point of fat are preferred because the signal from fat in the acquired data is at a minimum with respect to other views in the shot. View-ordering within each shot is usually determined such that the views having the most desirable characteristics are used to fill the central portions of k-space and such that signal modulations, e.g., that may be due to the evolution of magnetization throughout the shot, occur smoothly in k-space. For a multi-shot technique, most conventional 3D view-ordering schemes are not compatible with the need to arrange the views from each shot such that the more desirable views are encoded for the center of k-space. Accordingly, it would be desirable to provide a view-ordering strategy for a multi-shot 3D MRI data acquisition that encodes the more desirable views from each shot into the center of k-space and that is compatible with uniform parallel imaging, variable density (e.g., self-calibrated) parallel imaging, other variable density k-space sampling schemes and multi-shot pulse sequences having a transient signal, i.e., signal varies from shot to shot.

BRIEF DESCRIPTION OF THE INVENTION

In accordance with an embodiment, a method for acquiring magnetic resonance (MR) data using a multi-shot three-dimensional magnetic resonance imaging pulse sequence utilizing a plurality of shots to obtain MR data, includes defining a sampling pattern in a $k_y$-$k_z$ plane, the sampling pattern comprising a plurality of views in the $k_y$-$k_z$ plane, partitioning the $k_y$-$k_z$ plane into a plurality of blades, each blade having a blade size based on a target view value for the number of views to be contained in the blade, defining a blade ordering for the plurality of blades, defining a intra-shot view ordering for a set of views in each shot in the plurality of shots, the set of views including views corresponding to at least two blades and for each shot, acquiring the set of views based on the blade ordering and the intra-shot view ordering, wherein a signal level varies for at least two shots in the plurality of shots.

In accordance with another embodiment, a computer readable medium having computer executable instructions for performing a method for acquiring magnetic resonance (MR) data using a multi-shot three-dimensional magnetic resonance imaging pulse sequence utilizing a plurality of shots to obtain MR data, includes program code for defining a sampling pattern in a $k_y$-$k_z$ plane, the sampling pattern comprising a plurality of views in the $k_y$-$k_z$ plane, program code for partitioning the $k_y$-$k_z$ plane into a plurality of blades, each blade having a blade size based on a target view value for the number of views to be contained in the blade, program code for defining a blade ordering for the plurality of blades, program code for defining a intra-shot view ordering for a set of views in each shot in the plurality of shots, the set of views including views corresponding to at least two blades and program code for acquiring the set of views for each shot based on the blade ordering and the intra-shot view ordering, wherein a signal level varies for at least two shots in the plurality of shots.

In accordance with another embodiment, an apparatus for acquiring magnetic resonance (MR) data using a multi-shot three-dimensional magnetic resonance imaging pulse sequence utilizing a plurality of shots to obtain MR data, includes a magnetic resonance imaging assembly comprising a magnet, a plurality of gradient coils, at least one radio frequency coil, a radio frequency transceiver system and a pulse generator module and a controller coupled to the magnetic resonance imaging assembly and programmed to control the magnetic resonance imaging assembly to acquire magnetic resonance data using a multi-shot three-dimensional magnetic resonance imaging pulse sequence utilizing a plurality of shots to obtain the MR data. The controller is programmed to define a sampling pattern in a $k_y$-$k_z$ plane, the sampling pattern comprising a plurality of views in the $k_y$-$k_z$ plane, partition the $k_y$-$k_z$ plane into a plurality of blades, each blade having a blade size based on a target view value for the number of views to be contained in the blade, define a blade ordering for the plurality of blades, define a intra-shot view ordering for a set of views in each shot in the plurality of shots, the set of views including views corresponding to at least two blades and provide commands to the magnetic resonance imaging assembly to acquire the set of views for each shot based on the blade ordering and the intra-shot view ordering, wherein a signal level varies for at least two shots in the plurality of shots.

BRIEF DESCRIPTION OF THE DRAWINGS

Embodiments are illustrated by way of example and not limitation in the figures of the accompanying drawings, in which like reference numerals indicate corresponding, analogous or similar elements, and in which.

DETAILED DESCRIPTION

Figure 1:
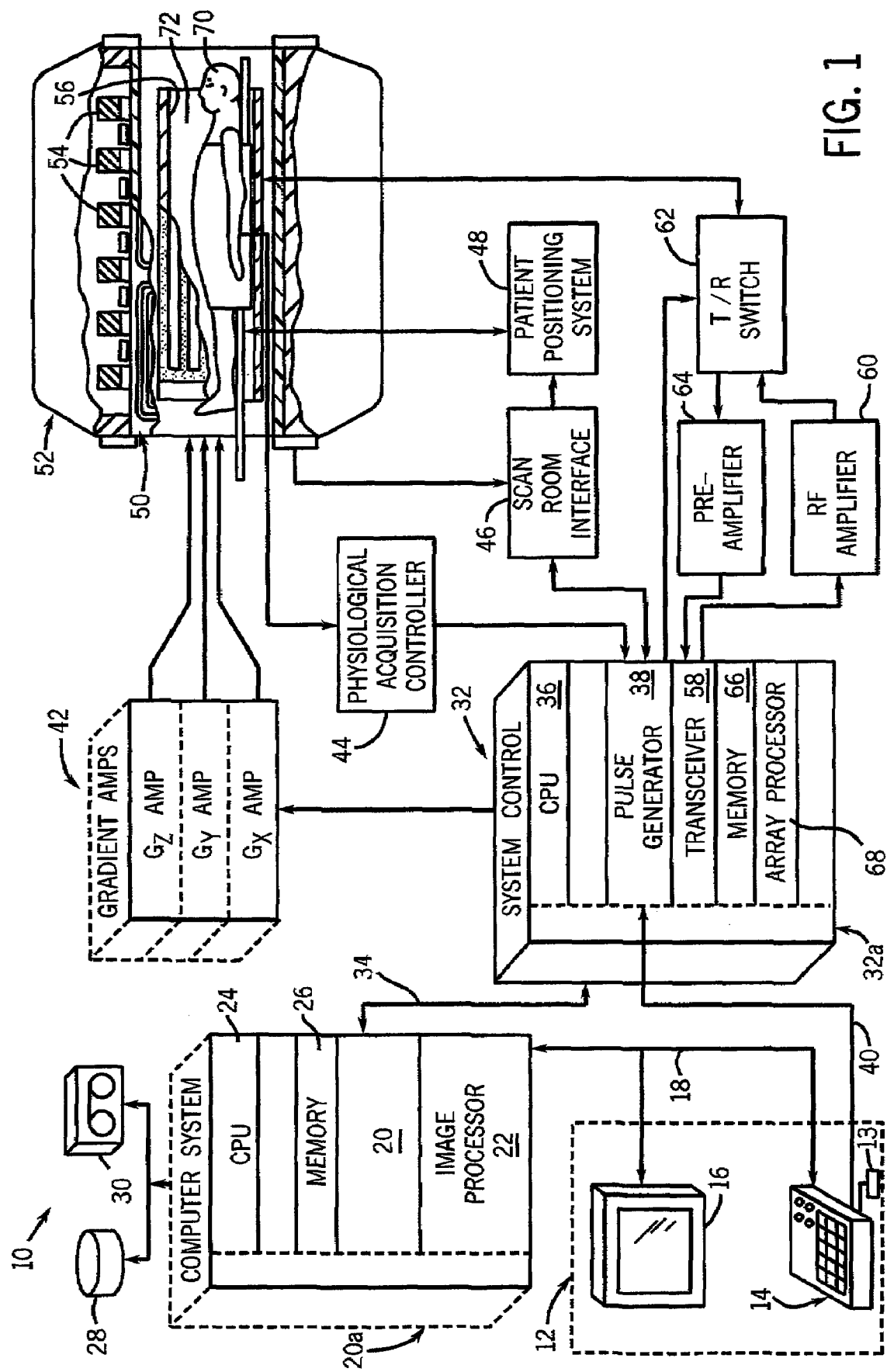
FIG. 1 is a schematic block diagram of an exemplary magnetic resonance imaging system in accordance with an embodiment.

In the following detailed description, numerous specific details are set forth in order to provide a thorough understanding of embodiments. However it will be understood by those of ordinary skill in the art that the embodiments may be practiced without these specific details. In other instances, well-known methods, procedures, components and circuits have not been described in detail so as not to obscure the embodiments.

A multi-shot three-dimensional (3D) magnetic resonance imaging (MRI) data view-ordering strategy for uniform density (e.g., for a parallel imaging technique) or variable density (e.g., for a self-calibrated parallel imaging technique, homodyne technique, etc.) k-space sampling schemes partitions a $k_y$-$k_z$ plane into multiple wedge-shaped "blades" (or radial fan beams). Variable density acquisition techniques sample the $k_y$-$k_z$ plane with a non-uniform pattern. Accordingly, the angular size of individual blades for a variable density acquisition technique may be adjusted according to the desired number of views for each blade. Each blade includes views near the origin of k-space that contain low-frequency information about the imaged object and high-frequency views farther away from the origin of k-space. Preferably, a single shot acquires views in at least two blades. The views in an individual blade may be acquired in a single shot or in multiple shots. Preferably, view-ordering within each shot is defined such that views having the most desirable characteristics are used to fill the central portions of k-space and such that signal modulations, e.g., that may be due to the evolution of magnetization throughout the shot, occur smoothly in k-space. However, any intra-shot view-ordering strategy may be used.

In one example application, an unwanted tissue signal selective inversion RF pulse may be prepended to a shot to provide spectral/spatial suppression in the images. In one example, the unwanted tissue signal is from fat. After the inversion RF pulse, the fat magnetization evolves during the shot such that views acquired at time points close to the null point of fat have better fat suppression. It is preferable to encode the views acquired at time points close to the null point of fat with $k_y$, $k_z$ values corresponding to the center of k-space such that most of the k-space energy that determines the image appearance has fat suppressed. For views that are acquired at time-points farther from the null point of fat, it is preferable to encode these views with $k_y$, $k_z$ values corresponding to the outer regions of k-space. In addition, it is preferable to fill k-space such that the magnitude of signal from fat varies smoothly throughout to avoid any discontinuities that cause artifacts in the reconstructed images. By partitioning (or segmenting) the $k_y$-$k_z$ plane into a plurality of blades, subsets of which correspond to individual shots, the view-ordering may be configured to encode more preferred views from each shot into the center of the $k_y$-$k_z$ plane and encode less preferred views into higher frequency portions of k-space.

FIG. 1 is a schematic block diagram of an exemplary magnetic resonance imaging system in accordance with an embodiment. The operation of MRI system 10 is controlled from an operator console 12 that includes a keyboard or other input device 13, a control panel 14 and a display 16. The console 12 communicates through a link 18 with a computer system 20 and provides an interface for an operator to prescribe MRI scans, display the resultant images, perform image processing on the images, and archive data and images. The computer system 20 includes a number of modules that communicate with each other through electrical and/or data connections, for example such as are provided by using a backplane 20a. Data connections may be direct wired links or may be fiber optic connections or wireless communication links or the like. The modules of computer system 20 may include an image processor module 22, a CPU module 24 and a memory module 26 that may include a frame buffer for storing image data arrays. In an alternative embodiment, the image processor module 22 may be replaced by image processing functionality on the CPU module 24. The computer system 20 is linked to archival media devices, such as disk storage 28 and tape drive 30, for storage of image data and programs and communicates with a separate system control computer 32 through a high speed serial link 34. Archival media include, but are not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which may be used to store the desired instructions and which can be accessed by computer system 20, including by internet or other computer network forms of access. The input device 13 can include a mouse, joystick, keyboard, track ball, touch activated screen, light wand, voice control, or any similar or equivalent input device, and may be used for interactive geometry prescription.

The system control computer 32 includes a set of modules in communication with each other via electrical and/or data connections 32a. Data connections 32a may be direct wired links, or may be fiber optic connections or wireless communication links or the like. In alternative embodiments, the modules of computer system 20 and system control computer 32 may be implemented on the same computer systems or a plurality of computer systems. The modules of system control computer 32 include a CPU module 36 and a pulse generator module 38 that connects to the operator console 12 through a communications link 40. The pulse generator module 38 may alternatively be integrated into the scanner equipment (e.g., magnet assembly 52). It is through link 40 that the system control computer 32 receives commands from the operator to indicate the scan sequence that is to be performed. The pulse generator module 38 operates the system components that play out (i.e., perform) the desired pulse sequence and produces data called RF waveforms which control the timing, strength and shape of the RF pulses to be used and the timing and length of the data acquisition window. The pulse generator module 38 connects to a gradient amplifier system 42 and produces data called gradient waveforms which control the timing and shape of the gradient pulses that are to be used during the scan. The pulse generator module 38 may also receive patient data from a physiological acquisition controller 44 that receives signals from a number of different sensors connected to the patient, such as ECG signals from electrodes attached to the patient. The pulse generator module 38 connects to a scan room interface circuit 46 that receives signals from various sensors associated with the condition of the patient and the magnet system. It is also through the scan room interface circuit 46 that a patient positioning system 48 receives commands to move the patient table to the desired position for the scan.

The gradient waveforms produced by the pulse generator module 38 are applied to gradient amplifier system 42 which is comprised of Gx, Gy and Gz amplifiers. Each gradient amplifier excites a corresponding physical gradient coil in a gradient coil assembly generally designated 50 to produce the magnetic field gradient pulses used for spatially encoding acquired signals. The gradient coil assembly 50 forms part of a magnet assembly 52 that includes a polarizing magnet 54 and a whole-body RF coil 56. A patient or imaging subject 70 may be positioned within a cylindrical patient imaging volume 72 of the magnet assembly 52. A transceiver module 58 in the system control computer 32 produces pulses that are amplified by an RF amplifier 60 and coupled to the RF coils 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered and digitized in the receiver section of the transceiver 58. The transmit/receive switch 62 is controlled by a signal from the pulse generator module 38 to electrically connect the RF amplifier 60 to the RF coil 56 during the transmit mode and to connect the preamplifier 64 to the coil during the receive mode. The transmit/receive switch 62 can also enable a separate RF coil (for example, a surface coil) to be used in either the transmit or receive mode.

The MR signals sensed by the RF coil 56 are digitized by the transceiver module 58 and transferred to a memory module 66 in the system control computer 32. Three dimensional (3D) MRI data is typically collected in a 3D Fourier space known in imaging as "k-space," a reciprocal space connected to real space via a Fourier transform. Typically, each MR signal, or "view," is encoded with a particular spatial frequency using "phase-encoding" and "slice-encoding" gradient pulses. For example, in a 3D Cartesian acquisition of MRI data, two directional phase encodings may be performed that correspond to a phase-encoding axis ($k_y$) and a slice-encoding axis ($k_z$). K-space is sampled by acquiring multiple phase- and slice-encoded views, each of which is defined by a unique $k_y$, $k_z$ position in the $k_y$-$k_z$ plane. Each view may acquire all the $k_x$ data for a specific pair of phase-encoding and slice-encoding values (i.e., each view may acquire all of the $k_x$ data required for its $k_y$, $k_z$ position). Multiple such digitized views are stored temporarily in the memory module 66 until they are subsequently transformed to create images. An array processor 68 uses a known transformation method, most commonly a Fourier transform, to create images from the MR signals. These images are communicated through the link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on display 16.

Figure 2:
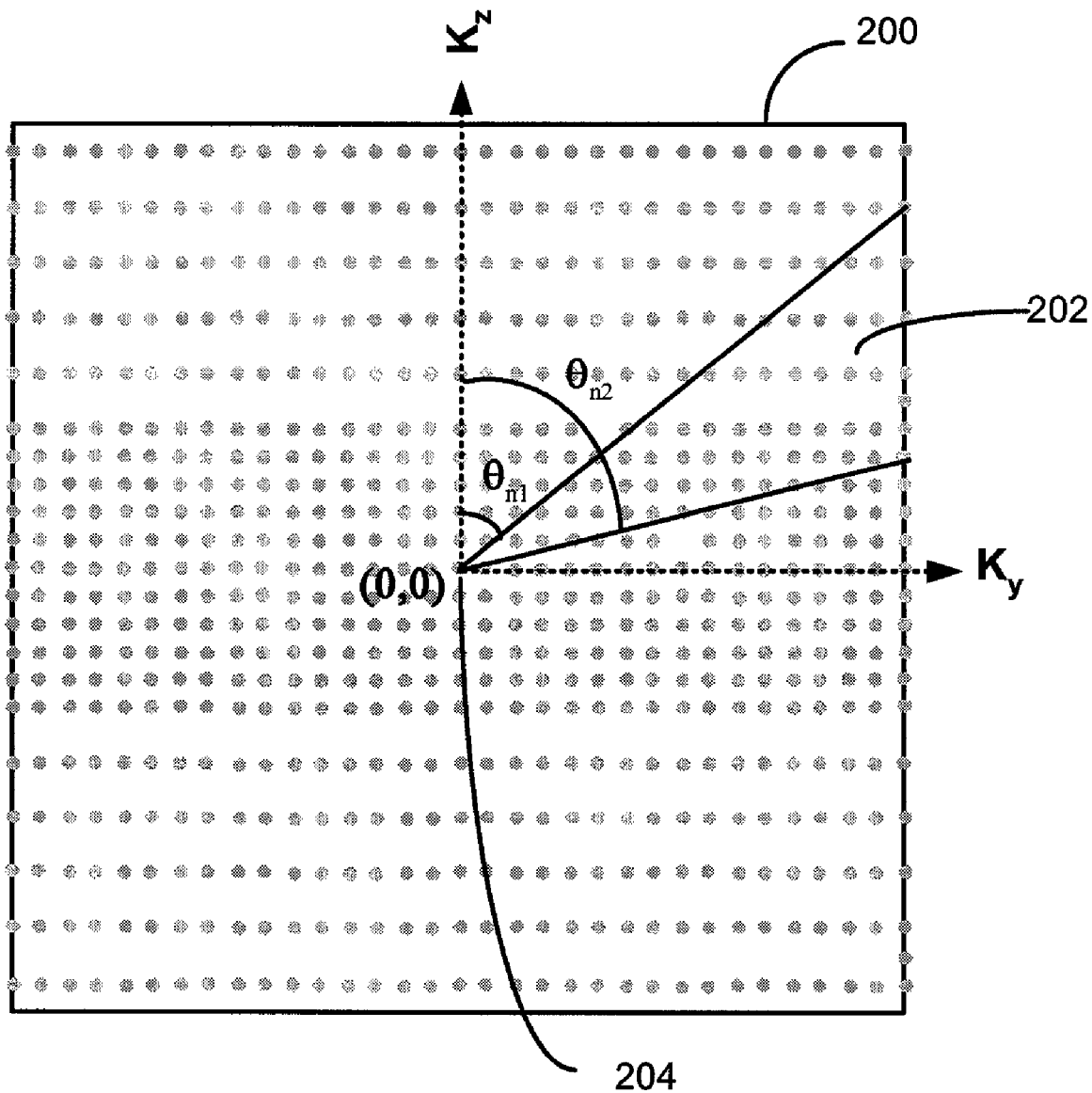
FIG. 2 is a schematic diagram showing a segmentation method for a $k_y$-$k_z$ plane for a variable density sampling pattern in accordance with an embodiment.
Figure 3:
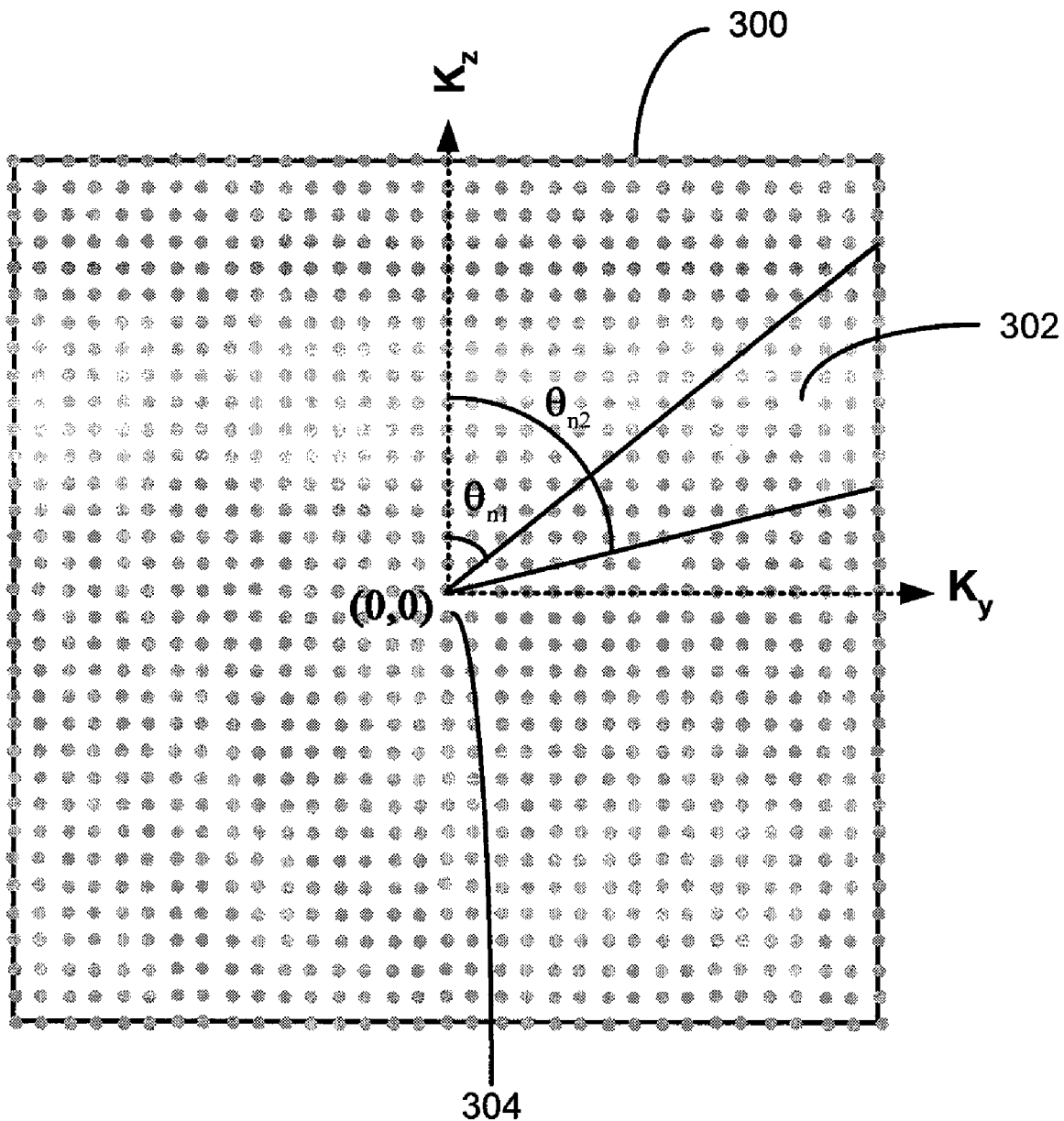
FIG. 3 is a schematic diagram showing an exemplary segmentation of a $k_y$-$k_z$ plane for a uniform density sampling pattern in accordance with an embodiment.

As mentioned, multiple views may be acquired, e.g., using an MRI system such as described above with respect to FIG. 1 or any similar or equivalent system for obtaining MR images, and transformed to create images. A view may acquire all the $k_x$ data required for full Nyquist sampling or a smaller fraction thereof for use with an incomplete sampling strategy including, but not limited to, a parallel imaging technique, a self-calibrated parallel imaging technique or a homodyne reconstruction technique. FIG. 2 is a schematic diagram showing a segmentation method for a $k_y$-$k_z$ plane for a variable density sampling pattern in accordance with an embodiment and shows an exemplary variable density sampling pattern for a 32×32 image matrix. FIG. 3 is a schematic diagram showing a segmentation method for a $k_y$-$k_z$ plane for a uniform density sampling pattern in accordance with an embodiment and shows an exemplary uniform density sampling pattern for a 32×32 image matrix. Referring to FIGS. 2 and 3, the location of each view in the $k_y$-$k_z$ plane 200, 300 may be described by a coordinate pair, $k_y$, $k_z$. Each view may acquire the $k_x$ data required for its $k_y$, $k_z$ position. A multi-shot acquisition uses multiple shots to acquire all necessary views for filling a k-space. To order the shots in k-space for the variable density sampling pattern, the $k_y$-$k_z$ plane 200, 300 may be partitioned (or segmented) into multiple wedge-shaped "blades" (or radial fan beams), each of which has thickness $Nk_x$ (the total number of $k_x$ points for each view). FIGS. 2 and 3 show an exemplary blade 202, 302. Each blade is bounded by radial lines at polar angles, $\theta_{n1}$, and $\theta_{n2}$ where n labels the blade number. Each blade contains both low-frequency and high-frequency $k_y$, $k_z$ lines. Each blade may touch the origin 204, 304 (i.e., point (0,0)) of the $k_y$-$k_z$ plane, however, the blade pattern may alternatively be offset from the origin by several k-space points without serious effect on the reconstructed images. In a variable density sampling pattern, the angular sizes of the individual blades may be adjusted based on the desired number of views per blade. It is not necessary for the number of views per blade to be equal for all blades, however, in applications where a steady-state condition for the magnetization is desirable, holding the number of views per shot constant is preferable. For some applications in which some acquired views are considered preferable to other views, it is desirable to encode the preferred views for points closer to the origin of the $k_y$-$k_z$ plane. Segmenting the $k_y$-$k_z$ plane into blades allows for preferred views from each shot to be encoded for the low-frequency lines in $k_y$-$k_z$ near the origin of the $k_y$-$k_z$ plane. In the case where each blade has $\theta_{n1}=\theta_{n2}$, the blades reduce to radial lines.

Figure 4:
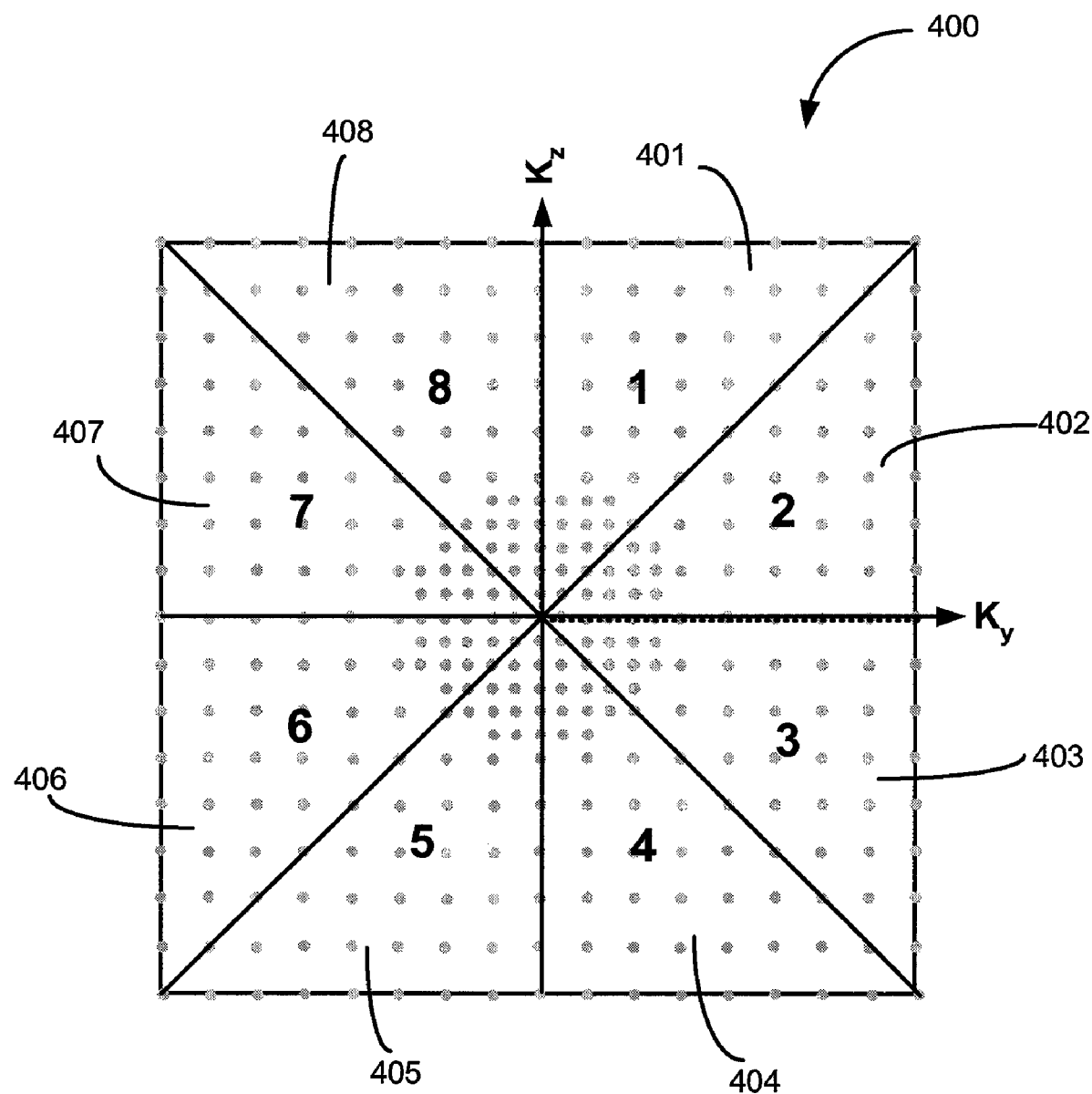
FIG. 4 is a schematic diagram showing an exemplary segmentation of a $k_y$-$k_z$ plane for a self-calibrated variable density sampling pattern in accordance with an embodiment.

FIG. 4 is a schematic diagram showing an exemplary segmentation of a $k_y$-$k_z$ plane for a self-calibrated variable density sampling pattern in accordance with an embodiment. As mentioned above, the segmentation scheme may also be used for a uniform density sampling pattern. In the exemplary variable density sampling pattern shown in FIG. 4, the center of k-space is fully sampled at the Nyquist frequency and the outer regions are undersampled. The variable density sampling pattern corresponds to an exemplary self-calibrated parallel imaging acquisition, in which the fully sampled region at the center of k-space is used to fill in the missing k-space data in the outer regions of k-space. Eight blades (blade 1 (401), blade 2 (402), blade 3 (403), blade 4 (404), blade 5 (405), blade 6 (406), blade 7 (407) and blade 8 (408)) are shown with equal angular size and with an equal number of views per blade. The number of blades used to partition the $k_y$-$k_z$ plane is determined by the desired number of views per shot, which is in turn determined by the desired length for each shot. The exemplary sampling pattern shown in FIG. 4 has 8-fold reflection symmetry. Therefore, dividing the $k_y$-$k_z$ plane into 2, 4, or 8 blades of equal angular size results in an equal distribution of views into each blade. Dividing the plane into a different number of blades would require adjustment of the individual blades' angular sizes if it is desirable to keep the number of views per blade constant. As mentioned above, alternatively, the number of views per blade does not need to be equal for all blades, the number of views can vary from blade to blade.

The blades may be acquired using any blade-ordering scheme, including, but not limited to, a sequential (or reverse sequential) ordering in which the blades are acquired in ascending (or descending) order from blade 1 (401) to blade 8 (408) (or from blade 8 (408) to blade 1 (401)); an interleaved ordering in which blades are acquired interleaved, for example, blade 1 (401), blade 3 (403), blade 5 (405), blade 7 (407), blade 2 (402), blade 4 (404), blade 6 (406), blade 8 (408), or other orderings in which the blade number is stepped using a constant increment; a conjugate pair ordering in which acquisition of a blade is followed by acquisition of its conjugate pair, for example, blade 1 (401) and blade 5 (405) are acquired first, then blade 2 (402) and blade 6 (406), then blade 3 (403) and blade 7 (407), followed by blade 4 (404) and blade 8 (408).

Figure 5:
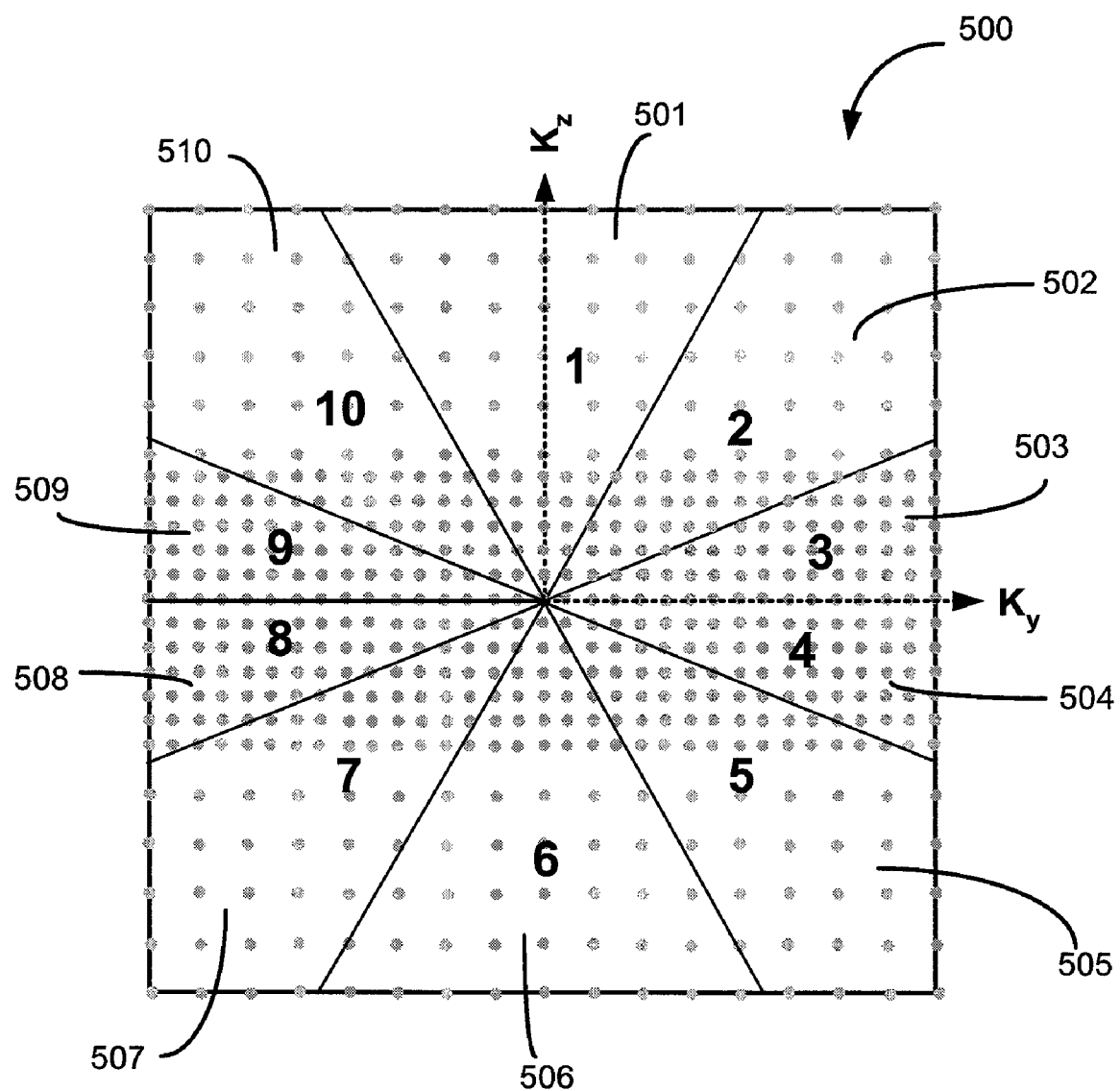
FIG. 5 is a schematic diagram showing an exemplary segmentation of a $k_y$-$k_z$ plane for a self-calibrated variable density sampling pattern in which a reduction factor R=2 for both the phase-encoding and slice-encoding directions in accordance with an embodiment.

FIG. 5 is a schematic diagram showing an exemplary segmentation of a $k_y$-$k_z$ plane for a self-calibrated variable density sampling pattern in which the reduction factor R=2 for both the phase-encoding and slice-encoding directions in accordance with an embodiment. In this exemplary embodiment, ten blades (blade 1 (501), blade 2 (502), blade 3 (503), blade 4 (504), blade 5 (505), blade 6 (506), blade 7 (507), blade 8 (508), blade 9 (509) and Blade 10 (510)) are shown partitioning (or segmenting) the $k_y$-$k_z$ plane 500 such that the number of views per blade is approximately constant. The angular size of the individual blades differs based on the view sampling density inside each blade. Blade 3 (503), blade 4 (504), blade 8 (508) and blade 9 (509), which have the highest sampling density, have the smallest angular sizes. Blade 1 (501) and blade 6 (506), which have the lowest sampling density, have the largest angular sizes. For this exemplary variable density sampling pattern, the total number of views to be acquired, 736, is not evenly divisible into 10 blades. This may be managed either by having an unequal number of views per shot or by having an equal number of views per shot wherein unnecessary views are discarded or not acquired.

Alternatively, a user may discard a number of views from the sampling pattern such that the total number of views to be acquired is evenly divisible by the desired number of blades. As mentioned above, alternatively, the number of views per blade does not need to be equal for all blades, the number of views can vary from blade to blade.

The segmentation of the $k_y$-$k_z$ plane for a uniform or variable density sampling pattern into blades (examples of variable density sampling pattern segmentations are shown in FIGS. 4 and 5) is compatible with multiple intra-shot view-orderings. For applications in which some acquired views in each shot are considered preferable to other views, the preferred views may be encoded for points close to the origin of the $k_y$-$k_z$ plane such that they contribute more to the overall image appearance than other views. By segmenting the $k_y$-$k_z$ plane into blades that each contain both low-frequency views and high-frequency views, it is possible to define an intra-shot view-ordering that places preferred views from each shot near the center of k-space, while avoiding discontinuities in k-space from placing views with very different amplitudes or phases next to each other.

For many applications, views acquired during a certain portion of a shot will be preferred relative to other views in the shot due to the state of the magnetization or the imaged object during that time. For example, some views in a shot may have a more desirable contrast between two tissues of interest (as for example, may be achieved using an inversion preparation pulse to create T1-weighting), better fat suppression, or better suppression of signal from localized regions within the imaging volume (as for example, may be achieved using "saturation bands"). When cardiac or respiratory gating is used to trigger the start of a shot, there is typically a preferred time window for acquiring views that corresponds to a period of relative quiescence in the imaged object. Frequently, the preferred views are acquired during a time window that occurs with the same relative timing in each shot. Views acquired outside this time window may become less preferred as they are acquired farther outside the time window. In some exemplary embodiments, a single time-point may be defined at which the magnetization or imaged object exhibits preferred characteristics. A single time-point may be thought of as a time window with the width of a delta function. In this application, the phrase "time window" also includes a single time-point, such as, for example, the null point of fat.

Figure 6:
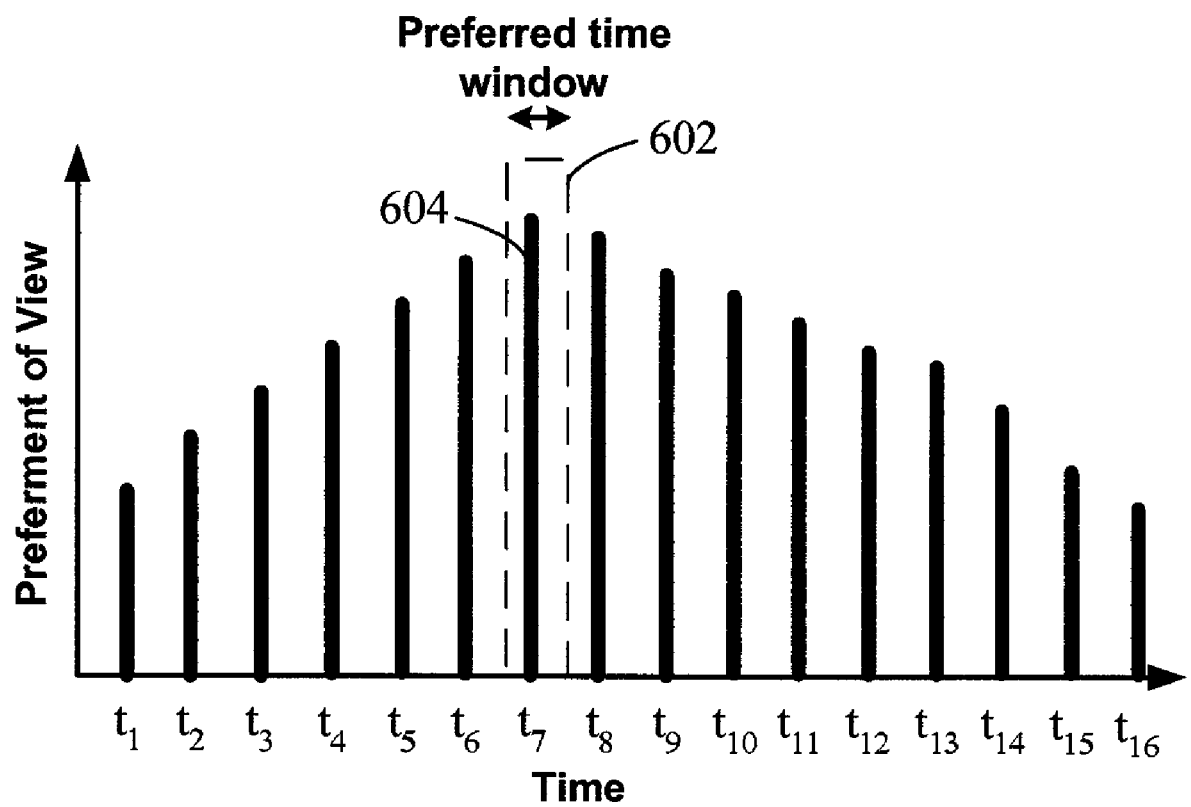
FIG. 6 is a schematic diagram showing a single shot that acquires multiple views of varying preferment in accordance with an embodiment.

FIG. 6 is a schematic diagram showing a single shot that acquires multiple views of varying preferment in accordance with an embodiment. In the example of FIG. 6, a preferred time window 602 near time $t_7$ is shown. Views collected during the preferred time window 602 are preferred relative to views acquired outside the preferred time window 602. The view 604 acquired at time $t_7$ is preferred relative to all other views in the shot. For views acquired prior to the preferred time window 602, the degree to which they are preferred (i.e., their "preferment") increases with decreasing time from the preferred time window 602. Likewise, for views acquired after the preferred time window 602, the degree to which they are preferred decreases with increasing time from the preferred time window 602.

The definition of a preferred time window depends on the particular imaging application and user preferences. For some clinical applications with fat suppression, for example, suppression of the signal from fat to 20% of the signal for water may be considered sufficient, while other applications may require suppression of the fat signal to lower levels. Some applications may be more sensitive to increased signal content from fat for views near the edges of k-space due, for example, to more high-frequency information in the images from multiple tissue interfaces.

For applications in which the magnetization is smoothly evolving during the shot, views acquired outside the preferred time window may become less preferred as the views are acquired farther away in time from the preferred time window. To determine an intra-shot view-ordering that places more preferred views closer to the origin of the $k_y$-$k_z$ plane: (1) a preferred time window during each shot may be identified; (2) a view (or multiple views) acquired during the preferred time window may be phase- and slice-encoded for a region near the center of the $k_y$-$k_z$ plane; (3) a group of views acquired before the preferred time window may be encoded such that views acquired farther from the preferred time window are phase- and slice-encoded for more distant locations in k-space compared to other views in this group; and (4) a group of views acquired after the preferred time window may be encoded such that views acquired farther from the preferred time window are phase- and slice-encoded for more distant locations in k-space compared to other views in this group. While it is preferable to arrange all views in each shot according to these conditions, it is not necessary to strictly obey these conditions. It is possible to encode some portion of the views required to fill k-space such that these conditions are not met without causing any significant effect in the reconstructed images, particularly in the high-frequency outer regions of k-space.

Figure 7:
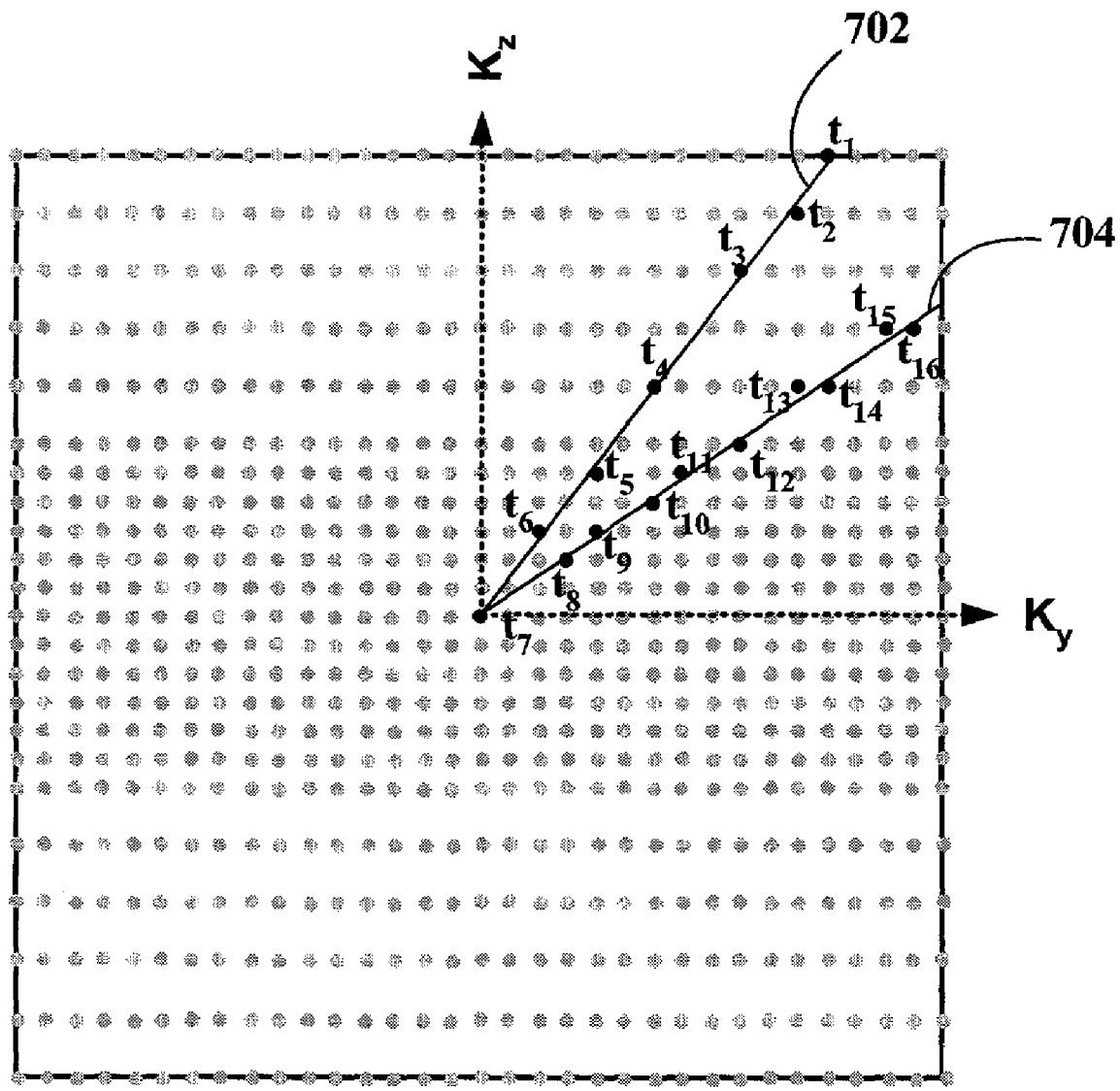
FIG. 7 shows an exemplary intra-shot view-ordering with IN-CENTER-OUT ordering for two radial lines in accordance with an embodiment.

As mentioned, the segmentation of the $k_y$-$k_z$ plane for a uniform or variable density sampling pattern into blades as described above with respect to FIGS. 2-6 is compatible with multiple intra-shot view orderings. FIG. 7 shows an exemplary IN-CENTER-OUT intra-shot view-ordering for two radial lines in accordance with an embodiment. IN-CENTER-OUT ordering encodes a first group of views such that the radial distance from the origin of the $k_y$-$k_z$ plane decreases with increasing time from the beginning of the shot, encodes a second group of views at or near the center of the $k_y$-$k_z$ plane, and encodes a third group of views such that the radial distance from the origin of the $k_y$-$k_z$ plane increases with increasing time from the beginning of the shot. FIG. 7 shows an exemplary intra-shot view ordering for a shot with 16 views in which the views have the preferment shown in FIG. 6. The most preferred view acquired at a time point $t_7$ is phase- and slice-encoded into a point at the origin of the $k_y$-$k_z$ plane. Views acquired at time points $t_1$ through $t_6$, prior to the preferred time window 602 (shown in FIG. 6) are encoded sequentially into points approximately along a radial line 702, such that their radial distance from the origin decreases as the time at which they are acquired approaches the preferred time window 602 (shown in FIG. 6). In this way, the views at $t_1$ through $t_6$ are ordered in k-space according to their preferment, with more preferred views encoded into points closer to the origin of the $k_y$-$k_z$ plane. Views acquired at time points $t_8$ through $t_{15}$, after the preferred time window 602 (shown in FIG. 6), are encoded into points approximately along a radial line 704 such that their radial distance from the origin increases as the time at which they are acquired increases after the preferred time window 602 (shown in FIG. 6).

Figure 8:
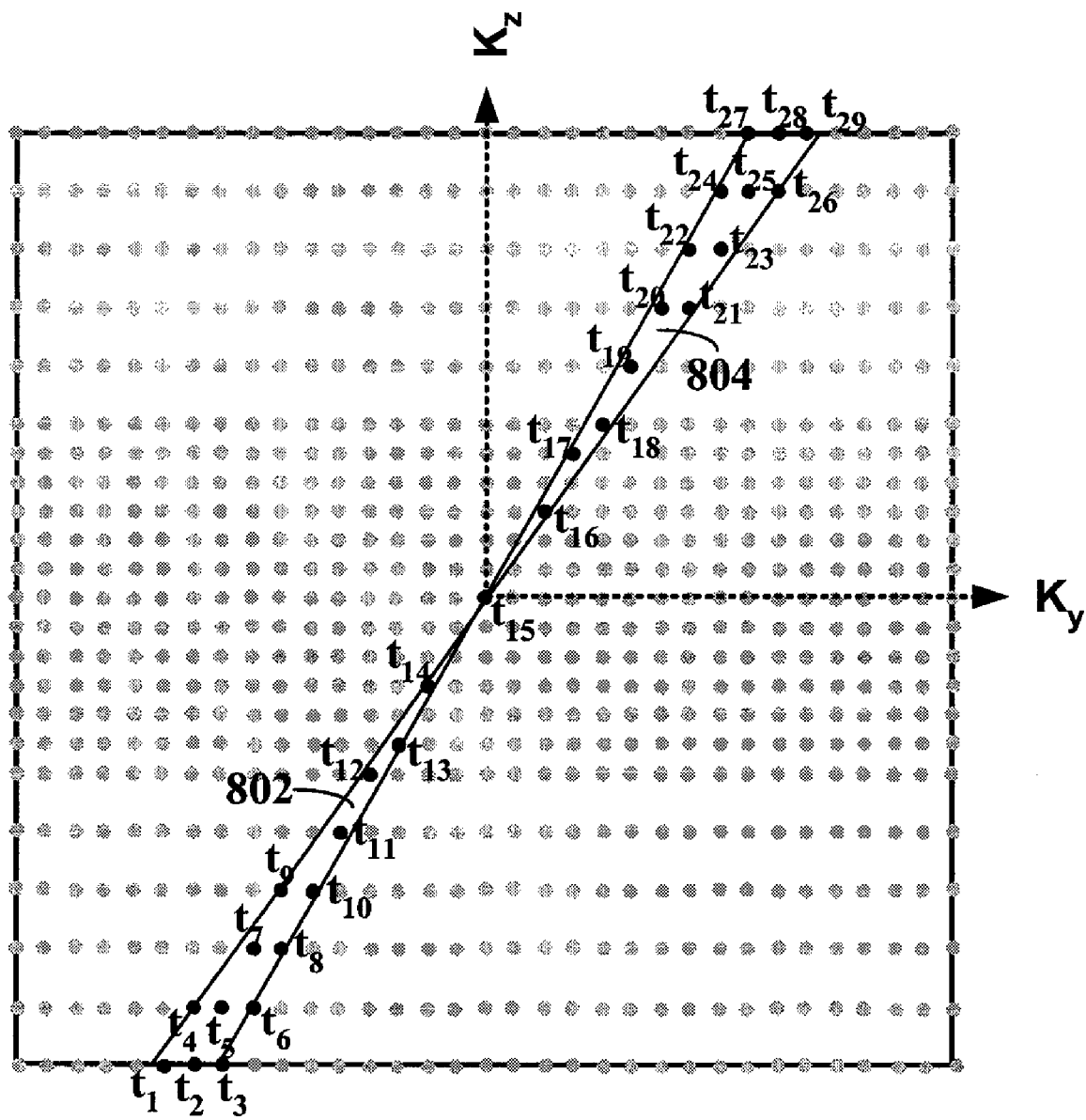
FIG. 8 shows an exemplary intra-shot view-ordering with IN-CENTER-OUT ordering in a conjugate pair of blades in accordance with an embodiment.

FIG. 8 shows an exemplary intra-shot view-ordering with IN-CENTER-OUT ordering in a conjugate pair of blades in accordance with an embodiment. In this exemplary intra-shot view-ordering, each shot acquires views for two separate blades, in which the blades are arranged as a conjugate pair. FIG. 8 illustrates an exemplary conjugate pair corresponding to one shot. In one embodiment, to completely fill the ky-kz plane, multiple shots may be used, each shot acquiring views for a different pair of blades. In this example, each shot acquires 29 views, and the 15$^{th}$ view acquired at time point $t_{15}$ is most preferred. The view acquired at $t_{15}$ is phase- and slice-encoded into a point at the origin of the ky-kz plane. Views acquired at time points $t_1$ through $t_{14}$ are encoded into blade 802 such that their radial distance from the origin decreases with view number (i.e., each subsequent view is encoded closer to the origin than the previous view). Views acquired at time points $t_{16}$ through $t_{29}$ are encoded into blade 804 such that their radial distance from the origin increases with view number.

In the example of FIG. 8, the middle view of the shot is preferred and the preceding views acquired at $t_1$ through $t_{14}$ may be used to completely fill blade 802 while the later views from $t_{16}$ through $t_{29}$ may be used to completely fill blade 804. In many applications, it is not necessary that the preferred view occur at the middle view of the shot, rather, the preferred view may occur closer to the beginning or end of the shot. For example, the preferred view may occur at the fifth time-point, $t_5$, near the beginning of the shot. In an exemplary embodiment, the angular sizes of both blades 802 and 804 may be increased to double the number of views contained in each blade. Views from pairs of shots may be used to fill blades 802 and 804 such that k-space is traversed in opposite directions by each shot of the pair. In the first shot of the pair, the views from $t_1$ through $t_4$ may be encoded into blade 802 such that the radial distance from the origin decreases with view number. Blade 802 is only sparsely filled by the first shot of the pair. The views from $t_6$ through $t_{29}$ of the first shot may be encoded into blade 804 such that the radial distance from the origin increases with view number. Blade 804 is almost completely filled by the first shot of the pair. For the second shot of the pair, the views from $t_1$ through $t_4$ may be encoded into blade 804 such that the radial distance from the origin decreases with view number, thereby completely filling blade 804. The views from $t_6$ through $t_{29}$ of the second shot may be encoded into blade 802 such that the radial distance from the origin increases with view number, thereby filling blade 802. The view from $t_5$ from both shots of the pair may be encoded near and/or into the origin and averaged, or one of the views from $t_5$ from the pair of shots may be discarded. By using pairs of shots to fill k-space wherein each shot traverses k-space in an opposite direction as its pair, variations in magnitude or phase that are periodic from shot-to-shot are compensated (i.e., balanced) by the two shots. It is not necessary that this view-ordering acquire views for conjugate paired blades in each shot. It is also possible to use this same IN-CENTER-OUT view-ordering scheme for any pair of blades.

Figure 9:
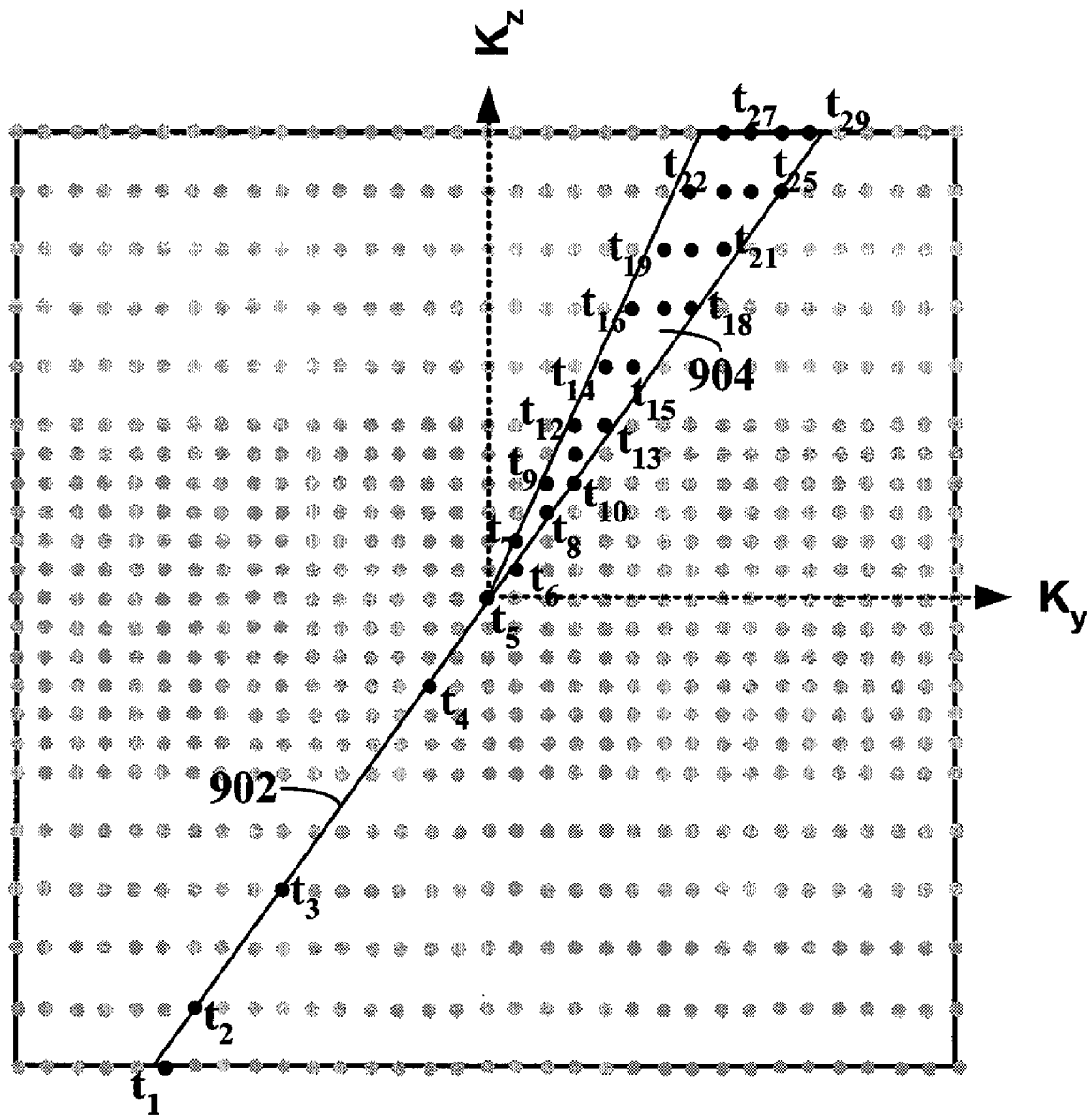
FIG. 9 shows an alternative exemplary intra-shot view-ordering with IN-CENTER-OUT ordering in a conjugate pair of blades in accordance with an embodiment.

In an alternative embodiment, the angular sizes of blade 802 and blade 804 may be individually adjusted to treat the situation where the preferred view occurs close to the beginning or end of the shot. FIG. 9 shows an alternative exemplary intra-shot view-ordering with IN-CENTER-OUT ordering in a conjugate pair of blades in accordance with an embodiment. Blade 902 contains 4 views and blade 904 contains 24 views. Views from time points $t_1$ through $t_4$ may be encoded into blade 902 such that the radial distance from the origin decreases with view number and views from time points $t_6$ through $t_{29}$ may be encoded into blade 904 such that the radial distance from the origin increases with view number. The view from time point $t_5$ is encoded into the origin. Not all acquired views are shown numbered in FIG. 9 for clarity.

Figure 10:
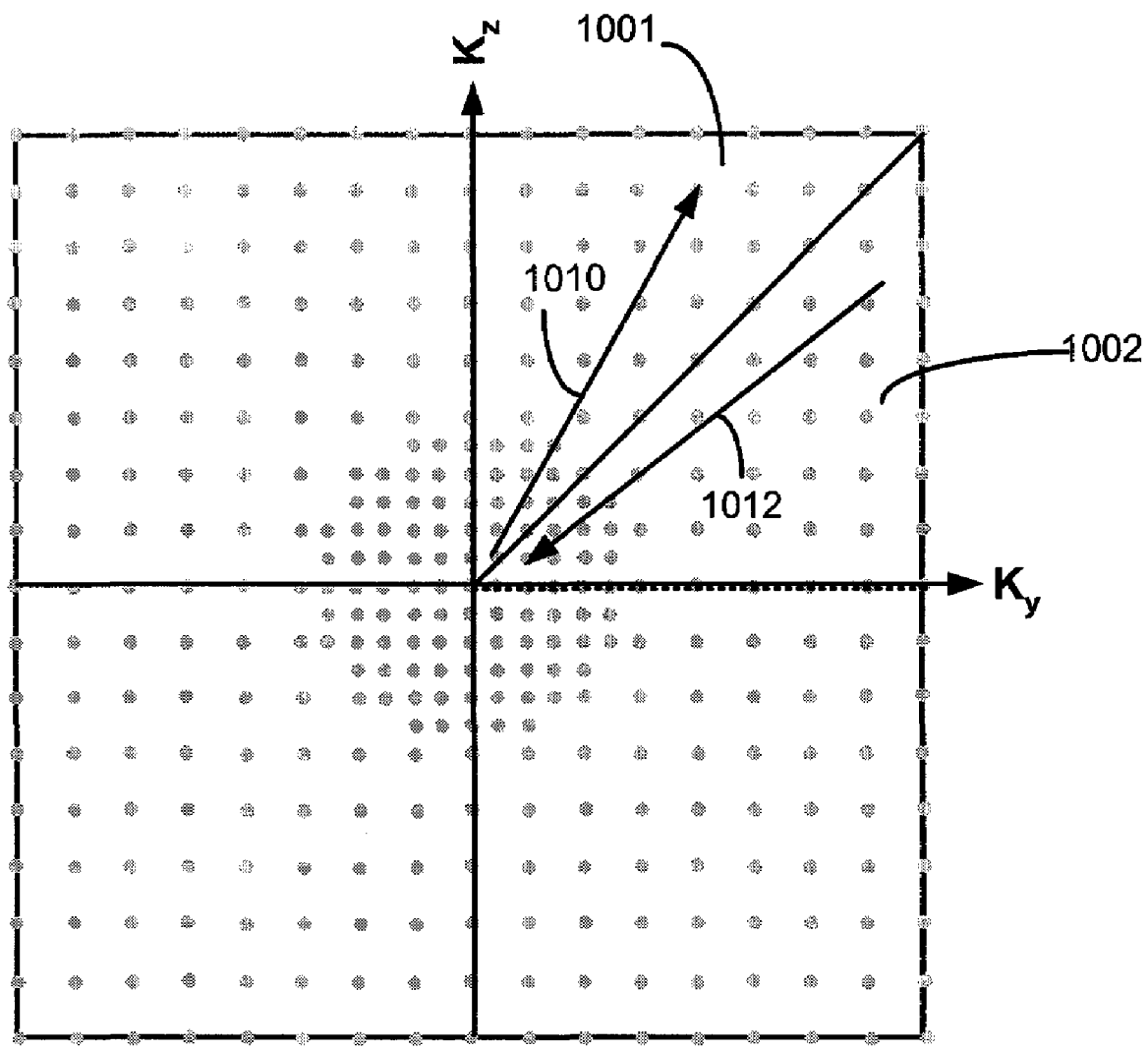
FIG. 10 shows an exemplary intra-shot view-ordering with CENTER-OUT-IN ordering for a pair of blades in accordance with an embodiment.

While IN-CENTER-OUT view orderings are preferred when a particular view or group of views from a shot is preferred, any alternative intra-shot view-orderings may be used with segmentation of the $k_y$-$k_z$ plane for a undersampled uniform or variable density sampling pattern into blades, including random or centric view-orderings. Centric view-ordering encodes the first acquired view in a shot into the center of the $k_y$-$k_z$ plane and each subsequent view is encoded into locations progressively farther from the $k_y$-$k_z$ plane origin. FIG. 10 shows an exemplary intra-shot view-ordering with CENTER-OUT-IN ordering for a pair of blades in accordance with an embodiment. In this exemplary intra-shot view ordering, each shot acquires views for two separate blades. CENTER-OUT-IN ordering encodes a first group of views at or near the center of the $k_y$-$k_z$ plane, encodes a second group of views such that the radial distance from the origin of the $k_y$-$k_z$ plane increases with increasing time from the beginning of the shot and encodes a third group of views such that the radial distance from the origin of the $k_y$-$k_z$ plane decreases with increasing time from the beginning of the shot. FIG. 10 illustrates an exemplary pair of blades, a first blade 1001 and a second blade 1002, corresponding to one shot. In this example, the first blade 1001 contains views encoded at or near the center of the $k_y$-$k_z$ plane and then encoded in an ascending order (as shown by arrow 1010) away from the origin of the $k_y$-$k_z$ plane and the second blade 1002 contains views encoded in a descending order (as shown by arrow 1012) towards the origin of the $k_y$-$k_z$ plane. In an embodiment, to completely fill the $k_y$-$k_z$ plane, multiple shots may be used, each shot acquiring views for a different pair of blades. While the blades shown in FIG. 10 are of equal size, as mentioned above, the angular size or number of views per blade does not need to be equal for all blades, the number of views can vary from blade to blade.

Figure 11:
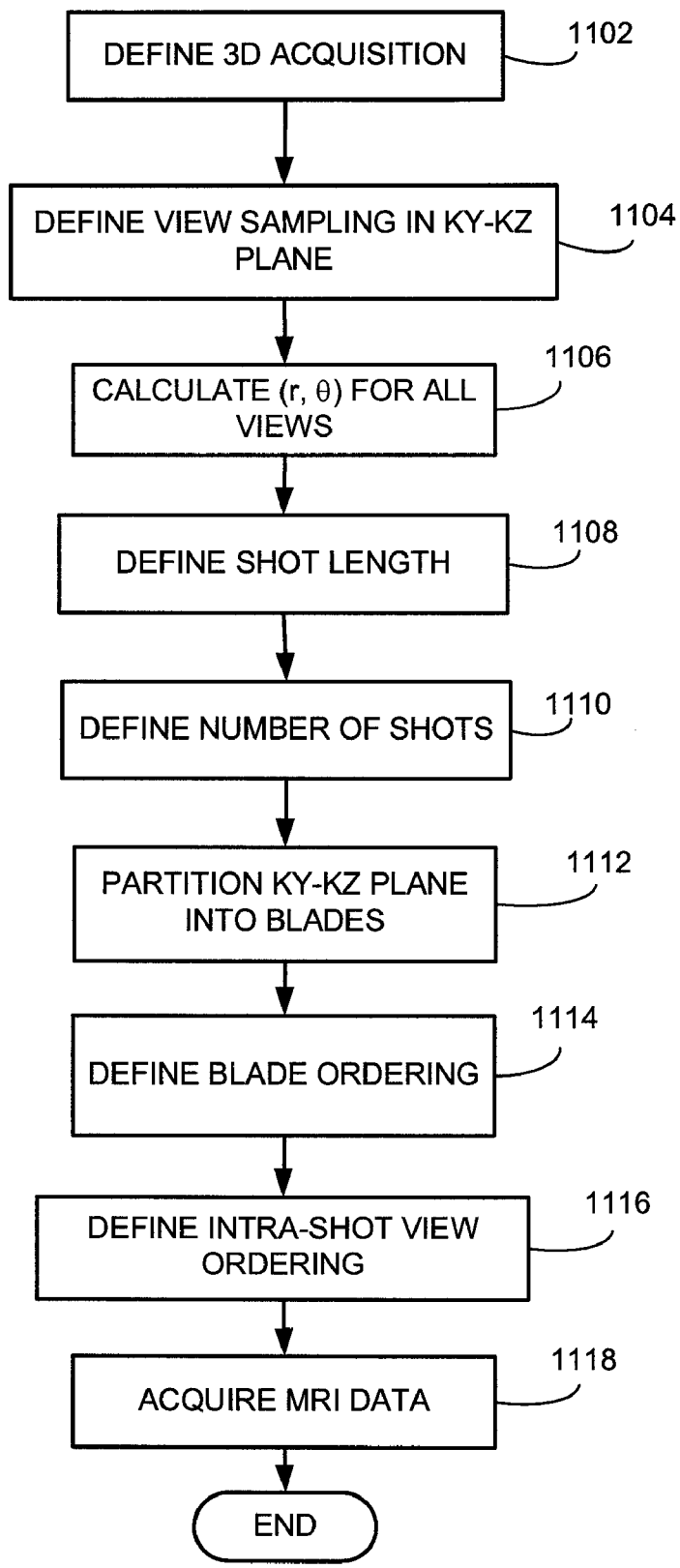
FIG. 11 is a flowchart illustrating a method for defining a multi-shot view-ordering for a 3D MRI data acquisition in accordance with an embodiment.

FIG. 11 is a flowchart illustrating a method for defining a multi-shot view-ordering for a 3D MRI data acquisition in accordance with an embodiment. At block 1102, a 3D acquisition is defined by selecting of a pulse sequence and by identifying (e.g., by a user) various scan parameters, for example, field of view and matrix size. The pulse sequence may be a pulse sequence in signal varies (e.g., transient) from shot to shot. Based on the various scan parameters, a sampling pattern in the $k_y$-$k_z$ plane is defined at block 1104. The sampling pattern may be a uniform or variable sampling pattern. First, views required to completely sample k-space at the Nyquist frequency are determined. Then a uniform or variable density sampling pattern that samples a subset of the k-space views required for complete Nyquist sampling is defined. In one example, a uniform sampling pattern may be defined in which every second line of $k_y$ is collected (i.e., a reduction factor (R) of 2). In another example, a variable density sampling pattern may be defined in which the central 16 lines of $k_y$ are fully sampled at the Nyquist frequency, but outside this central region, only every second line of $k_y$ is collected (i.e., $k_y$ is "undersampled" outside the central region with a reduction factor R=2). In an alternative embodiment, a non-Cartesian variable density sampling pattern may be defined that samples alternative views. The alternative views may later be re-sampled onto a Cartesian grid prior to Fourier transformation into image space. Another exemplary variable density sampling pattern collects views along interleaved curving arms that spiral outward from the origin of the $k_y$-$k_z$ plane. The acquired views may later be re-sampled onto a Cartesian grid and information about RF coil element sensitivities may be used to provide the missing information for Nyquist sampling using parallel imaging reconstruction techniques. Other variable density sampling patterns including, but not limited to arbitrary variable density sampling patterns may also be defined at block 1004.

At block 1106, a polar angle, θ, and a distance from the center of k-space, r, are calculated or otherwise determined for each view ($k_z$,$k_y$) defined by the sampling pattern (defined at block 1104). The location of each view in the $k_y$-$k_z$ plane may be described by a coordinate pair ($k_y, k_z$). A polar angle, $\theta$, for each view may be calculated relative to the $k_z$ axis in radians (0-2$\pi$) or in degrees (0-360), where $\theta$=arctan ($k_y/k_z$) or arctan ($k_z/k_y$). The radial distance from the center (i.e., the point (0,0)) of k-space, r, for each view ($k_y, k_z$) may be calculated using $r=(k_y^2+k_z^2)^{1/2}$.

At block 1108, a shot length is defined which may be limited by the length of a time window in which data having acceptable characteristics may be acquired. For example, cardiac gating may be used to acquire data during diastole in order to reduce motion artifacts in the reconstructed images. The shot length may therefore be limited to the time window that the user can confidently identify as diastole. It is not necessary for each shot to have equal length, as measured in units of time. Nor is it necessary for each shot to acquire an equal number of views. However, for many applications, a steady-state condition of the magnetization is desirable from shot-to-shot, and an efficient way to establish a steady-state condition is by using shots of equal length that acquire an equal number of views. Typically, if it is desirable to acquire an unequal number of views per shot, an equal number of alpha RF pulses are played out during each shot to maintain the steady-state condition and unwanted views are discarded, or simply not acquired, thereby maintaining a constant shot length. At block 1110, the total number of shots necessary to acquire all the views for the sampling pattern (defined at block 1104) is determined.

At block 1112, k-space is partitioned or segmented into at least two blades as described above with respect to FIGS. 2-6. For applications where it is desirable to hold the number of views per shot constant, unequal angular sizes may be used for each blade. At block 1114, a blade ordering (i.e., the order with which the blades defined at block 1112 are to be acquired) is defined. Any blade-ordering strategy may be used and it is not necessary for a single shot to acquire all the views in a blade.

At block 1116, an intra-shot view ordering is defined. The intra-shot view ordering may be based on a preferment of each view and the radial distance (r) of each view in the $k_y$-$k_z$ plane from the origin. The intra-shot view ordering may be determined such that views acquired inside a preferred time window are encoded into the $k_y$-$k_z$ plane in a region near the origin. At block 1118, MRI data is acquired according to the blade ordering determined at block 1114 and the intra-shot view-ordering determined at block 1116. Images are reconstructed from the k-space data.

The method described above is compatible with multiple pulse sequences including, but not limited to, pulse sequences in which signal varies (i.e., a transient signal) from shot to shot (or sample to sample), such as inversion recovery sequences in which multiple samples are acquired between inversion pulses, intermittent spectral saturation or inversion sequences in which multiple samples are acquired between chemically selective pulses, Fast Spin Echo (FSE) sequences in which multiple samples are acquired during the time in which relaxation is occurring, variable flip angle sequences in which signal varies due to variation in excitation flip angle, variable flip angle sequences in which signal varies simultaneously due to the variation in excitation or refocusing flip angle and due to relaxation or echo planar sequences in which signals vary due to relaxation and precession. In one example, a 3D gradient echo (GRE) pulse sequence with unwanted tissue signal selective inversion pulses prepended to one or more shots may be used to provide spectral/spatial suppression in reconstructed images. The degree of spectral/spatial suppression in a view may be used to determine its preferment. For example, in a sequence where it is desired to suppress the signal from fat, views acquired near the null point of fat are most preferred because the fat is most suppressed for these views. Using the method described above with respect to FIG. 10, views acquired with such a pulse sequence may be encoded such that views having better fat suppression are encoded for positions nearer the origin in the $k_y$-$k_z$ plane and such that the fat suppression varies smoothly throughout k-space. Alternatively, an inversion RF pulse may be used to create a desired magnetization between two or more tissues of interest. For example, an inversion RF pulse may be used to create a desirable contrast between gray and white matter in the brain. The magnetization from gray matter and from white matter evolves during each shot of a multi-shot sequence and certain views during the shot will be more preferred due to the particular contrast between gray and white matter at the time of that view. The method of FIG. 10 may also be used to determine a view-ordering scheme that places the preferred views nearer the center of k-space for applications using inversion pulses to create tissue contrast.

In yet another example, a 3D Fast Spin Echo (FSE) sequence with reduced refocusing flip angles (i.e., less that 180°) may be used. Using the exemplary method described in FIG. 11, an intra-shot view ordering may be determined (block 1116, FIG. 11) that encodes the views acquired with the most desirable tissue contrast closer to the center of k-space. The reconstructed image contrast is thereby most strongly weighted by the views with the most desirable tissue contrast. For 3D FSE sequences with reduced refocusing flip angles, the desired T2-weighting typically occurs much later in the echo train than for a conventional FSE sequence due to the contribution to signal from stimulated echoes. By partitioning the $k_y$-$k_z$ plane (block 1112, FIG. 11) into blades that include views near or at the center of k-space, the method provides a way to fill the lower frequency part of k-space with views having the most desirable tissue contrast from each shot, and also provides a way to ensure that signal and phase variations among views acquired during each shot modulate k-space smoothly, without creating discontinuities.

Computer-executable instructions for determining a view-ordering for a multi-shot 3D acquisition according to the above-described method may be stored on a form of computer readable media. Computer readable media includes volatile and nonvolatile, removable and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by MRI system 10 (shown in FIG. 1), including by internet or other computer network forms of access.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:

1. A method for acquiring magnetic resonance (MR) data using a multi-shot three-dimensional magnetic resonance imaging pulse sequence utilizing a plurality of shots to obtain MR data, the method comprising:
   defining a sampling pattern in a $k_y$-$k_z$ plane, the sampling pattern comprising a plurality of views in the $k_y$-$k_z$ plane;
   partitioning the $k_y$-$k_z$ plane into a plurality of blades, each blade having a blade size based on a target view value for the number of views to be contained in the blade;
   defining a blade ordering for the plurality of blades;
   defining a intra-shot view ordering for a set of views in each shot in the plurality of shots, the set of views including views corresponding to at least two blades; and
   for each shot, acquiring the set of views based on the blade ordering and the intra-shot view ordering;
   wherein a signal level varies for at least two shots in the plurality of shots.

2. A method according to claim 1, wherein the sampling pattern is a uniform density parallel imaging sampling pattern.

3. A method according to claim 1, wherein the sampling pattern is a variable density sampling pattern.

4. A method according to claim 1, wherein the plurality of blades includes at least a first blade having a first target view value and a second blade having a second target view value, wherein the first target value and the second target value are equal.

5. A method according to claim 1, wherein the plurality of blades includes at least a first blade having a first target view value and a second blade having a second target view value, wherein the first target value and the second target value are different.

6. A method according to claim 1, wherein the plurality of blades includes at least a first blade having a first angular size and a second blade having a second angular size, wherein the first angular size and the second angular size are equal.

7. A method according to claim 1, wherein the plurality of blades includes at least a first blade having a first angular size and a second blade having a second angular size, wherein the first angular size and the second angular size are different.

8. A method according to claim 1, wherein defining a sampling pattern further comprises determining a value of $k_y$ and a value of $k_z$ for each of the plurality of views in the $k_y$-$k_z$ plane to define a location in the $k_y$-$k_z$ plane for each of the plurality of views.

9. A method according to claim 8, wherein defining a sampling patter further comprises calculating a radial distance from an origin point of the $k_y$-$k_z$ plane for each of the plurality of views in the $k_y$-$k_z$ plane.

10. A method according to claim 1, wherein the multi-shot three-dimensional magnetic resonance imaging pulse sequence is a multi-shot three-dimensional gradient echo pulse sequence.

11. A method according to claim 10, wherein the multi-shot three-dimensional gradient echo pulse sequence comprises an inversion RF pulse prepended to at least one shot.

12. A method according to claim 10, wherein the multi-shot three-dimensional gradient echo pulse sequence comprises cardiac triggering.

13. A method according to claim 10, wherein the multi-shot three-dimensional gradient echo pulse sequence comprises respiratory triggering.

14. A method according to claim 1, wherein the multi-shot three-dimensional magnetic resonance imaging pulse sequence is a three-dimensional fast spin echo pulse sequence.

15. A method according to claim 1, wherein the intra-shot view ordering is IN-CENTER-OUT.

16. A method according to claim 1, wherein the intra-shot view ordering is CENTER-OUT-IN.

17. A method according to claim 1, wherein the intra-shot view ordering encodes preferred views into positions in the $k_y$-$k_z$ plane near an origin of the $k_y$-$k_z$ plane.

18. A computer readable medium having computer executable instructions for performing a method for acquiring magnetic resonance (MR) data using a multi-shot three-dimensional magnetic resonance imaging pulse sequence utilizing a plurality of shots to obtain MR data, the computer readable medium comprising:
   program code for defining a sampling pattern in a $k_y$-$k_z$ plane, the sampling pattern comprising a plurality of views in the $k_y$-$k_z$ plane;
   program code for partitioning the $k_y$-$k_z$ plane into a plurality of blades, each blade having a blade size based on a target view value for the number of views to be contained in the blade;
   program code for defining a blade ordering for the plurality of blades;
   program code for defining a intra-shot view ordering for a set of views in each shot in the plurality of shots, the set of views including views corresponding to at least two blades; and
   program code for acquiring the set of views for each shot based on the blade ordering and the intra-shot view ordering;
   wherein a signal level varies for at least two shots in the plurality of shots.

19. A computer readable medium according to claim 18, wherein the sampling pattern is a uniform density parallel imaging sampling pattern.

20. A computer readable medium according to claim 18, wherein the sampling pattern is a variable density sampling pattern.

21. A computer readable medium according to claim 18, wherein the intra-shot view ordering is IN-CENTER-OUT.

22. A computer readable medium according to claim 18, wherein the intra-shot view ordering is CENTER-OUT-IN.

23. A computer readable medium according to claim 18 wherein the intra-shot view ordering encodes preferred views into positions in the $k_y$-$k_z$ plane near an origin of the $k_y$-$k_z$ plane.

24. An apparatus for acquiring magnetic resonance (MR) data using a multi-shot three-dimensional magnetic resonance imaging pulse sequence utilizing a plurality of shots to obtain MR data, the apparatus comprising:
   a magnetic resonance imaging assembly comprising a magnet, a plurality of gradient coils, at least one radio frequency coil, a radio frequency transceiver system and a pulse generator module; and
   a controller coupled to the magnetic resonance imaging assembly and programmed to control the magnetic resonance imaging assembly to acquire magnetic resonance data using a multi-shot three-dimensional magnetic resonance imaging pulse sequence utilizing a plurality of shots to obtain the MR data, the controller further programmed to:
   define a sampling pattern in a $k_y$-$k_z$ plane, the sampling pattern comprising a plurality of views in the $k_y$-$k_z$ plane;

partition the $k_y$-$k_z$ plane into a plurality of blades, each blade having a blade size based on a target view value for the number of views to be contained in the blade;
define a blade ordering for the plurality of blades;
define a intra-shot view ordering for a set of views in each shot in the plurality of shots, the set of views including views corresponding to at least two blades; and provide commands to the magnetic resonance imaging assembly to acquire the set of views for each shot based on the blade ordering and the intra-shot view ordering;
wherein a signal level varies for at least two shots in the plurality of shots.

* * * * *